United States Patent
Mohanty

(10) Patent No.: US 11,020,359 B2
(45) Date of Patent: Jun. 1, 2021

(54) METHOD, COMPOSITIONS AND DEVICE FOR NANO-ENHANCED OPTO-CHEMICAL TRANS-DIFFERENTIATION OF CELLS AND TISSUES

(71) Applicant: Nanoscope Technologies LLC, Bedford, TX (US)

(72) Inventor: Samarendra Kumar Mohanty, Arlington, TX (US)

(73) Assignee: Nanoscope Technologies LLC, Bedford, TX (US)

(*) Notice: Subject to any disclaimer, the term of this patent is extended or adjusted under 35 U.S.C. 154(b) by 0 days.

(21) Appl. No.: 16/215,578

(22) Filed: Dec. 10, 2018

(65) Prior Publication Data
US 2019/0175524 A1   Jun. 13, 2019

Related U.S. Application Data

(60) Provisional application No. 62/596,864, filed on Dec. 10, 2017.

(51) Int. Cl.
| | | |
|---|---|---|
| B82Y 5/00 | (2011.01) | |
| A61K 31/12 | (2006.01) | |
| A61K 31/06 | (2006.01) | |
| A61K 31/404 | (2006.01) | |
| A61K 31/352 | (2006.01) | |
| A61P 27/02 | (2006.01) | |
| A61K 31/519 | (2006.01) | |
| G02F 1/365 | (2006.01) | |

(52) U.S. Cl.
CPC .............. *A61K 31/12* (2013.01); *A61K 31/06* (2013.01); *A61K 31/352* (2013.01); *A61K 31/404* (2013.01); *A61K 31/519* (2013.01); *A61P 27/02* (2018.01); *B82Y 5/00* (2013.01); *G02F 1/365* (2013.01)

(58) Field of Classification Search
None
See application file for complete search history.

(56) References Cited

PUBLICATIONS

Alghazali, K.M., Newby, S., Nima, Z.A. et al. Functionalized gold nanorod nanocomposite system to modulate differentiation of human mesenchymal stem cells into neural-like progenitors. Sci Rep 7, 16654 (2017). (Year: 2017).*

Denu RA, Nemcek S, Bloom DD, et al. Fibroblasts and Mesenchymal Stromal/Stem Cells are Phenotypically Indistinguishable. Acta Haematol. 2016; 136(2):85-97. (Year: 2016).*

(Continued)

*Primary Examiner* — Aurora M Fontainhas
(74) *Attorney, Agent, or Firm* — CrossPond Law

(57) ABSTRACT

The present invention relates to novel nanomaterial-molecular compositions, methods and devices thereof for efficient and targeted trans-differentiation of cells including fibroblasts and glia into neurons, both in vitro as well as in situ and in-vivo, which is of great importance for cell replacement therapies. Specifically, the invention provides a nanomaterial-molecular composition, device and method for targeted nano-enhanced opto-chemical trans-differentiation of fibroblasts/glia to neurons in the central and peripheral nervous system for restoration of neural functions in patients by delivery of nanomaterial-molecular composition, followed by optical illumination.

12 Claims, 10 Drawing Sheets

(56) References Cited

PUBLICATIONS

Yu Zhang et al., "Small Molecules, Big Roles—the Chemical Manipulation of Stem Cell Fate and Somatic Cell Reprogramming," J Cell Sci 125, No. 23 (2012): 5609-20.

Danwei Huangfu et al., "Induction of Pluripotent Stem Cells by Defined Factors is Greatly Improved by Small-Molecule Compounds," Nature Biotechnology 26 (Jun. 22, 2008): 795.

Esther Y Son et al., "Conversion of Mouse and Human Fibroblasts into Functional Spinal Motor Neurons," Cell Stem Cell 9, No. 3 (2011): 205-18.

Eva C Thoma et al., "Chemical Conversion of Human Fibroblasts into Functional Schwann Cells," Stem Cell Reports 3, No. 4 (2014): 539-47.

Jem A Efe et al., "Conversion of Mouse Fibroblasts into Cardiomyocytes Using a Direct Reprogramming Strategy," Nature Cell Biology 13, No. 3 (2011): 215.

John W McDonald et al., "Transplanted Embryonic Stem Cells Survive, Differentiate and Promote Recovery in Injured Rat Spinal Cord," Nature Medicine 5, No. 12 (1999): 1410.

Lin Cheng et al., "Generation of Neural Progenitor Cells by Chemical Cocktails and Hypoxia," Cell Research 24 (Mar. 18, 2014): 665.

Lin Cui et al., "Transplantation of Embryonic Stem Cells Improves Nerve Repair and Functional Recovery after Severe Sciatic Nerve Axotomy in Rats," Stem Cells 26, No. 5 (2008): 1356-65.

M Baranek et al., "Effect of Small Molecules on Cell Reprogramming," Molecular BioSystems 13, No. 2 (2017): 277-313.

Peter Riess et al., "Transplanted Neural Stem Cells Survive, Differentiate, and Improve Neurological Motor Function after Experimental Traumatic Brain Injury," Neurosurgery 51, No. 4 (2002): 1043-54.

Sayaka Sekiya and Atsushi Suzuki, "Direct Conversion of Mouse Fibroblasts to Hepatocyte-like Cells by Defined Factors," Nature 475, No. 7356 (2011): 390.

Thomas Vierbuchen et al., "Direct Conversion of Fibroblasts to Functional Neurons by Defined Factors," Nature 463, No. 7284 (2010): 1035.

Walter Heine et al., "Transplanted Neural Stem Cells Promote Axonal Regeneration through Chronically Denervated Peripheral Nerves," Experimental Neurology 189, No. 2 (2004): 231-40.

Wang P J, Chen S Q, Huang M, Liu C L, Shen Y Y, Cai Q, "Differentiation of Induced Pluripotent Stem Cells into Neural Stem Cells Induced by Brain-Derived Neurotrophic Factor via Wnt/$\beta$-Catenin and Extracellular Signal-Regulated Kinase/Mitogen-Activated Protein Kinases Signal Pathway," Zhonghua Yi Xue Za Zhi 97, No. 41 (2017): 3263-68.

Wenxiang Hu et al., "Direct Conversion of Normal and Alzheimer's Disease Human Fibroblasts into Neuronal Cells by Small Molecules," Cell Stem Cell 17, No. 2 (2015): 204-12.

Xiang Li et al., "Small-Molecule-Driven Direct Reprogramming of Mouse Fibroblasts into Functional Neurons," Cell Stem Cell 17, No. 2 (2015): 195-203.

Xin Xie, Yanbin Fu, and Jian Liu, "Chemical Reprogramming and Transdifferentiation," Current Opinion in Genetics & Development 46 (2017): 104-13.

Xinxin Han et al., "Efficient and Fast Differentiation of Human Neural Stem Cells from Human Embryonic Stem Cells for Cell Therapy," Stem Cells International 2017 (2017).

Yanqin Li et al., "Generation of IPSCs from Mouse Fibroblasts with a Single Gene, Oct. 4, and Small Molecules," Cell Research 21, No. 1 (2011): 196.

\* cited by examiner

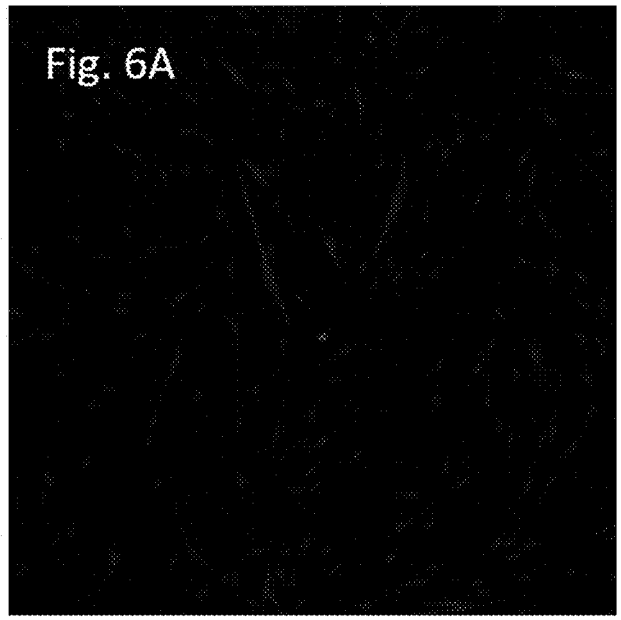
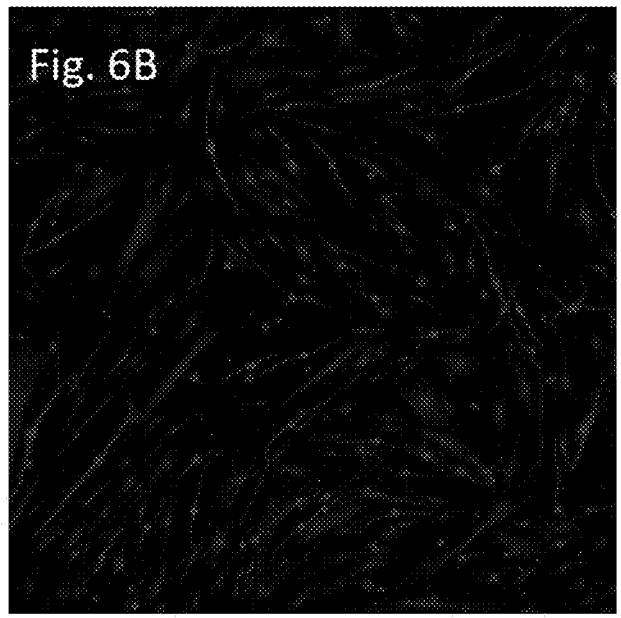

METHOD, COMPOSITIONS AND DEVICE FOR NANO-ENHANCED OPTO-CHEMICAL TRANS-DIFFERENTIATION OF CELLS AND TISSUES

CROSS-REFERENCE

This application claims the benefit of U.S. provisional application No. 62/596,864 filed Dec. 10, 2017 which application is incorporated herein by reference.

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

STATEMENT REGARDING FEDERALLY SPONSORED RESEARCH OR DEVELOPMENT

This invention was made with funding by NanoScope Technologies, LLC. The Government has no rights in the invention.

FIELD OF THE INVENTION

The present invention relates generally to novel compositions, devices and methods for trans-differentiation of fibroblasts/glia to neurons, both in vitro as well as in situ, and in-vivo which is of great importance for cell replacement therapies. Specifically, the invention provides unique nanomaterial-molecular compositions, devices and methods for targeted nano-enhanced opto-chemical trans-differentiation of fibroblasts/glia to neurons in the central and peripheral nervous system for restoration of neural functions in patients by delivery of nanomaterial-molecular composition, followed by optical illumination.

BACKGROUND OF THE INVENTION

Injury to the central nervous system including spinal cord, brain and retina as well as peripheral nervous system leads to irreversible loss of neurons and the disruption of neural pathways, resulting in severe impairments of sensory and motor function.

Brain Injury is defined as an alteration in brain function, or other evidence of brain pathology, caused by an external force, or acquired or degenerative. Millions of individuals live with a long-term disability as a result of brain injuries, the annual cost of which to the society exceeds hundreds of billions of USD. Incidence of spinal cord injury (SCI) exceeds millions of individuals. SCI leads to irreversible neuronal loss and glial scar formation, which ultimately result in persistent neurological dysfunction. In addition, several millions individuals suffer from transected peripheral nerve injury (PNI). Stress on a repaired nerve can also result from surrounding tissue edema.

Cell transplantation using stem or differentiated cells has shown as a potential therapeutic strategy for neuronal injuries. The use of cells derived from human fetal tissues (e.g., embryonic stem cells) suffers from immunological rejection and ethical controversies. Therefore, induced pluripotent stem cells (iPSCs) from a patient's somatic cells are being pursued. Recent studies have shown that the transplanted neural stem cells (NSCs) can achieve neuronal outgrowth and functional repair. (1-5)

However, transplantation-based cell therapy faces two major difficulties for treating nerve injuries in human patients; (i) potential for tumor formation from undifferentiated stem cells exist in the injury site; and (ii) significant time delay in preparation of stem cells for autologous transplantation, not optimal for functional improvement.

As an alternative to transplantation, reprogramming of endogenous non-neuronal cells, such as scar-forming fibroblasts/glia into neurons has been attempted. In this method, the fates of many somatic cells (in-vitro) are re-specified by the forced expression of a few transcription factors. (6,7)

Neuronal conversion from human fibroblasts can be induced by lineage-specific transcription factors (6); however, the introduction of ectopic genes limits the therapeutic applications of such approach. Direct conversion of fibroblasts into neurons (bypassing the neural progenitor stage) has also been shown by different chemical cocktails of small molecules (8-16). The Small molecules provide a number of compelling advantages such as rapid and reversible biological effects, tunable synthetic chemistry to allow functional optimization. Further, relative ease of preparation, handling and administration etc makes them more practical for in-vitro and in-vivo applications. However, current trans-differentiation using small molecules technologies are limited by: (i) low trans-differentiation efficiency; (ii) requirement of long trans-differentiation period and (iii) lack of spatially-controlled trans-differentiation.

SUMMARY OF THE INVENTION

To meet the challenges, the present invention provides novel compositions, methods and devices for nano-enhanced opto-chemical trans-differentiation (NOCT) method to achieve spatially targeted trans-differentiation of fibroblasts/glia to neurons with high efficiency in a short time period for in-vitro and in-situ applications.

In a preferred embodiment, the invention provides a nanomaterial-molecular composition for NOCT consisting of (i) Curcumin; (ii) 2,4-Dinitrophenol, (iii) SB216763; (iv) SD-208; (v) PD98059; and (vi) Nanomaterials including nanoparticles (spheres, rods, ellipsoids, pyramids) made of metal, semiconductor or insulators (e.g., polymers), which may be biodegradable.

In an embodiment, the present invention provides a method for efficient and targeted NOCT of cells in-vitro, in-situ or in-vivo which comprises of: providing functionalized nanomaterial-molecular compositions to a population of cells, whereby said nanomaterials binds to the cell type of interest; and providing optical illumination of said population of cells with a light beam tuned to activation of said nanomaterials by photothermal, photochemical or photo-disruption, whereby said cell types bound by said functionalized nanomaterials allow release and/or delivery of said molecular compositions into said cell type.

In addition, the invention in some aspects provides devices for targeted nano-enhanced opto-chemical trans-differentiation (NOCT) of fibroblasts/glia to neurons in the central and peripheral nervous system for restoration of neural functions in subjects diagnosed with disorders of CNS and PNS system by actuating delivery of nanomaterial-molecular composition, followed by optical illumination.

In yet another embodiment, this invention demonstrates that NOCT of fibroblast to neurons is achieved in an efficient and spatially targeted manner using a near-infrared (NIR)

laser beam. In-situ NOCT is achieved by injection of nano-material-molecular composition followed by shining of the NIR laser beam in targeted areas.

According to another aspect of the invention, this invention clearly demonstrate that the NOCT method is a viable, efficient and fast approach to achieve trans-differentiation of targeted fibroblasts/glia to functional neurons.

According to another aspect of the invention, the disclosed invention provides a device and method for the use of NOCT for trans-differentiation of fibroblast/glial scar(s) formed around implant to functional neurons in the central nervous system.

In another embodiment, the present disclosure also provides a device and method for nano-enhanced opto-chemical trans-differentiation of fibroblast/glial scars formed in injuries for example in injured spinal cord to functional neurons.

According to yet another aspect, the present disclosure provides a device and method for nano-enhanced opto-chemical trans-differentiation of fibroblast scars formed around implants in the peripheral nervous system to functional neurons.

In a broader aspect, the disclosure provides methods and devices for reliable in-vitro, in-situ or in-vivo trans-differentiation of different cell types to targeted cell types by use of different molecular compositions, and for use in treatment of variety of disorders. The disorders that find use of the compositions, methods and devices described herein include but not limited to strokes, Traumatic Brain Injury (TBI), nerve-machine interfaces, deep-brain-stimulation implant devices, neuro-degenerative brain disorders, spinal cord injury, and peripheral nerve injury, retinal degenerative diseases including but not limited to Retinitis Pigmentosa, Leber's congenital amaurosis, Dry-age related macular degeneration and Retinal Dystrophy.

It is contemplated that any embodiment of a method, device or composition described herein can be implemented with respect to any other method, device or composition described herein.

Details associated with the embodiments described above and others are described below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

Next, we show an example of use of gold nano-rods and NIR laser beam for NOCT.

Here, the figure illustrates the use of NOCT for trans-differentiation of fibroblasts to neurons. FIG. 6A shows the immunostained (Blue: DAPI; Red: βIII tubulin) cells treated with chemicals showing significant number of non-transdifferentiated fibroblasts. FIG. 6B shows the immunostained (Blue: DAPI; Red: βIII tubulin) cells treated with gold nanorods, chemicals and nanosecond near-infrared laser beam, demonstrating high efficient trans-differentiation to neurons.

8070: Regenerating axons of neurons trans-differentiated from Glial/Fibroblasts using NOCT.

Figure 9:
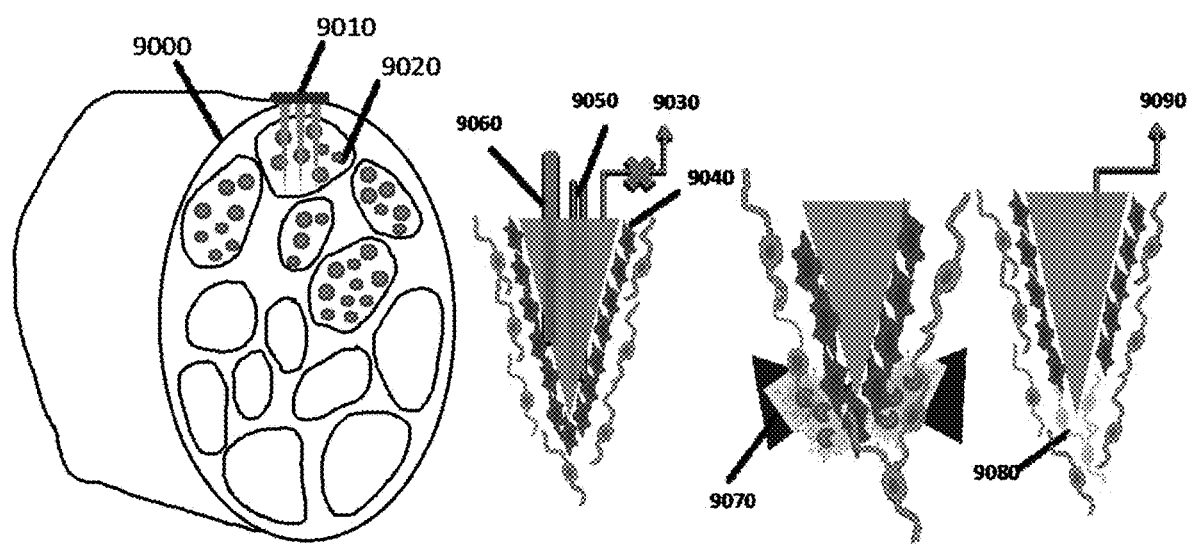

FIG. 9 represents various components of the device and method for spatially targeted Nano-enhanced Opto-Chemical Trans-differentiation (NOCT) in peripheral nervous system. 9000: Cross-section of peripheral nerve; 9010: Implanted electrode-nerve interface; 9020: Peripheral nerve axon; 9030: Electrode(s) for electrical stimulation/detection; 9040: Neural activity measurement and/or stimulation is blocked by glia/fibroblast scar; 9050: Cannula port for delivery of fluid containing chemicals and/or nano-materials; 9060: Optical fiber for light delivery/signal detection; 9070: Light illumination (400-1500 nm); 9080: Transdifferentiated Neuron from Glia/Fibroblast, and 9090: Neural activity measurement/stimulation is allowed via trans-differentiated neurons from glia/fibroblasts using NOCT.

Figure 10:
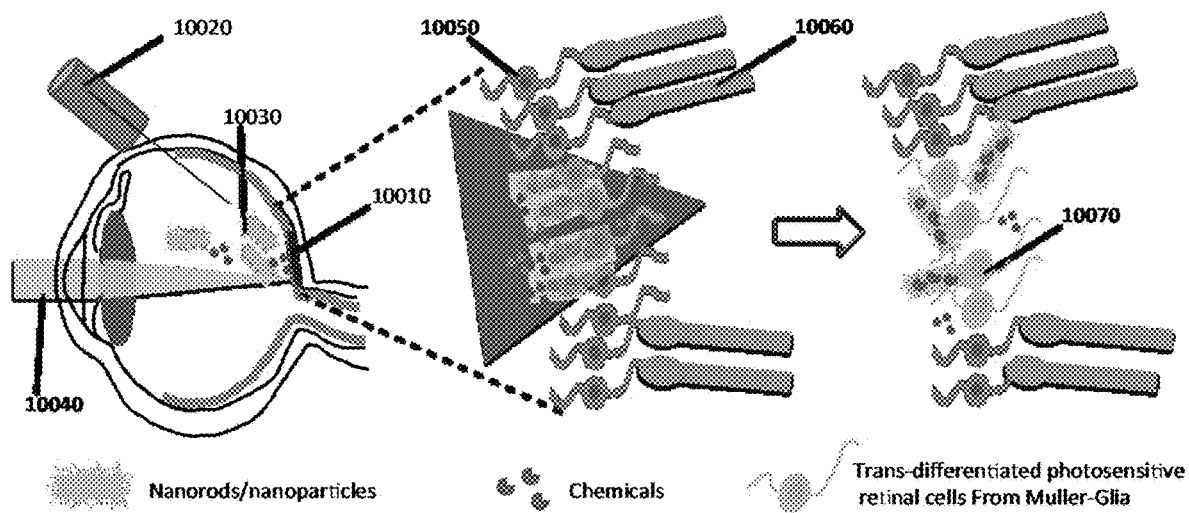

FIG. 10 shows various steps of the spatially targeted in-situ Nano-enhanced Opto-Chemical Trans-differentiation (NOCT) of Mueller Glial cells to photosensitive retinal cells in retina. 10010: Degenerated/scarred retina,
10020: Device for delivering nanoparticles/chemicals,
10030: Nanoparticles and chemicals,
10040: Laser beam (400-1500 nm),
10050: Muller-Glial cells,
10060: Natural photoreceptors,
10070: Trans-differentiated photosensitive retinal cells from Muller-glia using in-situ NOCT.

Figure 11A:
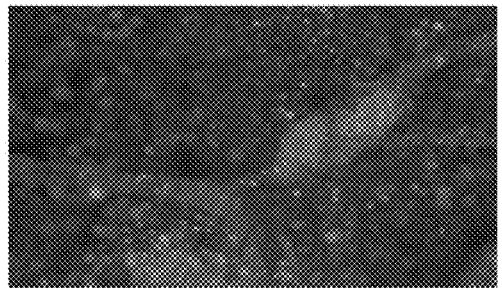
Figure 11B:
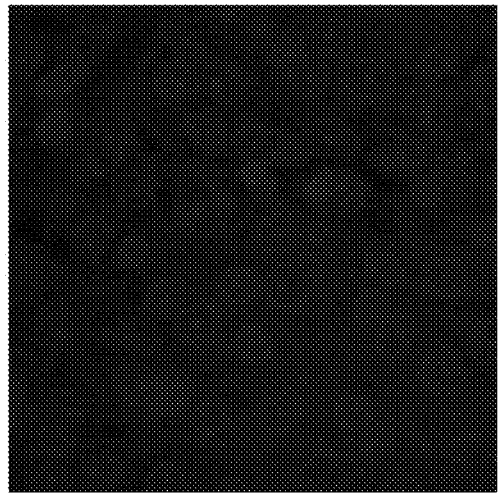

FIG. 11A shows In-situ trans-differentiation of Muller Glial cells to partially trans-differentiated photoreceptor like cells (ptdPRs) in rd1 mice. Nuclei stained with DAPI (blue) and partially trans-differentiated PRs in retina are immunostained with visual arrestin antibody (green). FIG. 11B shows negative control showing retinal cell nuclei stained with DAPI (blue) and absence of photoreceptor like cells (visual arrestin in green) in rd1 mice.

Figure 12:
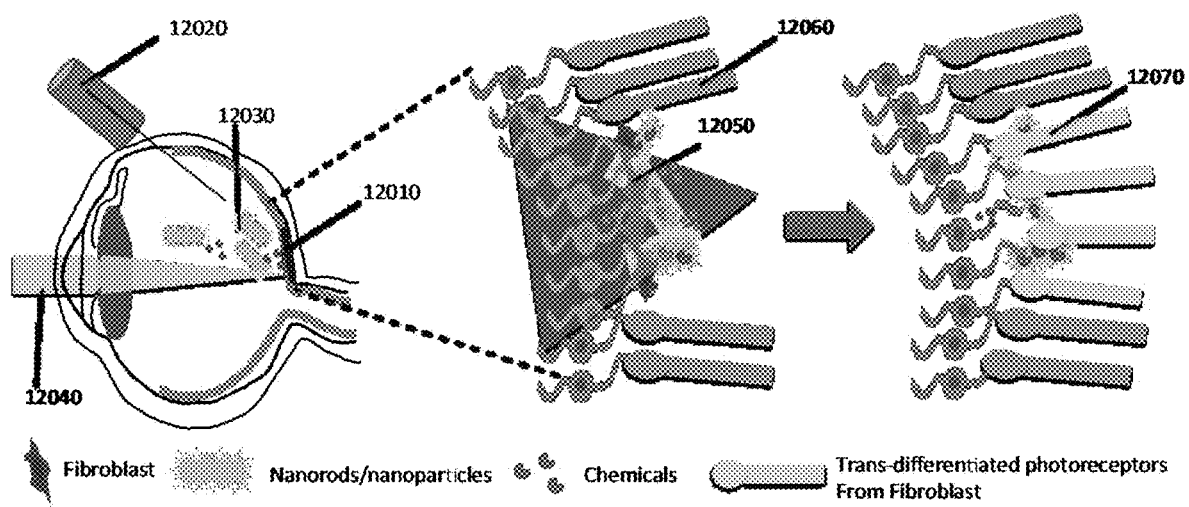

FIG. 12 shows various steps of the spatially targeted in-situ Nano-enhanced Opto-Chemical Trans-differentiation (NOCT) of fibroblasts to photoreceptors in retina.
12010: Degenerated/scarred retina,
12020: Device for delivering nanoparticles/chemicals,
12030: Nanoparticles and chemicals,
12040: Laser beam (400-1500 nm),
12050: Fibroblasts in scarred retina,
12060: Natural photoreceptors,
12070: Trans-differentiated photoreceptors from fibroblasts using in-situ NOCT.

Figure 13:
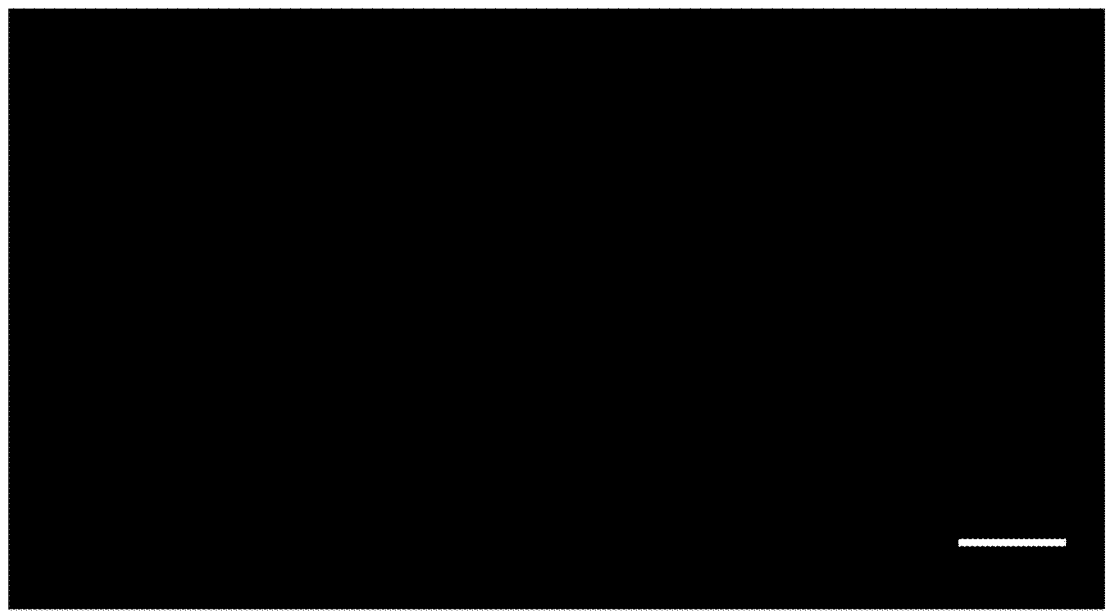

FIG. 13 shows in-situ trans-differentiated photoreceptor like cells (ptdPRs) in rd1 mice. Nuclei stained with DAPI (blue) and partially trans-differentiated PRs in retina are immunostained with visual arrestin antibody (green). Scale bar: 20 μm.

Figure 14:
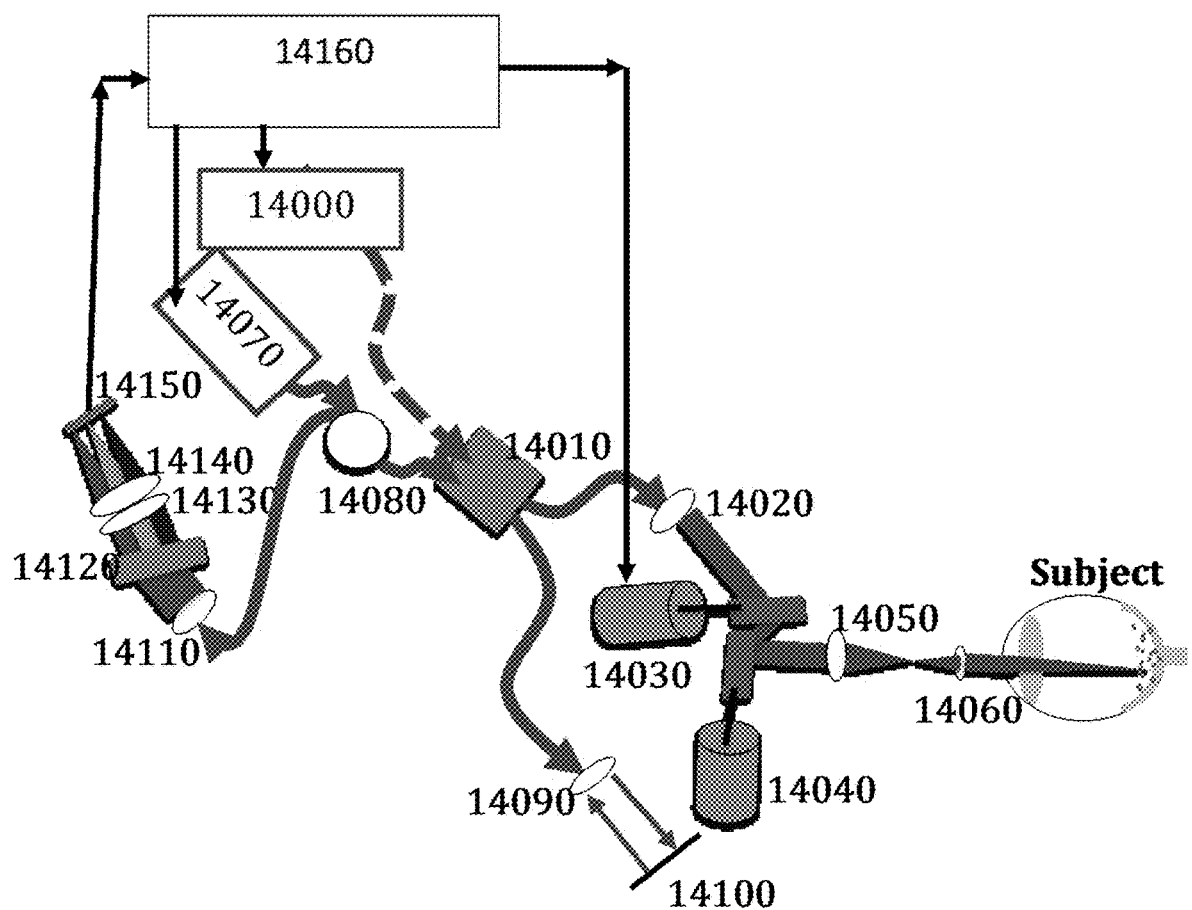

FIG. 14 shows the Schematic of integrated device for NOCT and imaging by OCT. 14000: Visible/NIR laser; 14010: Fiber coupler; 14020: collimating lens-1; 14030, 14040: scanning mirrors; 14050, 14060: Lens pair; 14070: low coherence source; 14080: Circulator; 14090: collimating lens-2; 14100: reference mirror; 14110: collimating lens-3; 14120: grating; 14130, 14140: lens pair; 14150: camera; 14160: Computer, display and controller.

DETAILED DESCRIPTION OF THE INVENTION

Cell transplantation using stem or differentiated cells has shown as a potential therapeutic strategy for injuries caused to central or peripheral nervous system. The use of cells derived from human fetal tissues (e.g., embryonic stem cells (5)) suffers from immunological rejection and ethical controversies. Therefore, induced pluripotent stem cells (iPSCs) from a patient's somatic cells are being pursued (17). Terminally differentiated somatic cells have been reprogrammed to iPSCs by forced expression of a set of transcription factors. Recent studies have shown that the transplanted neural stem cells (NSCs) can achieve neuronal outgrowth and functional repair. However, transplantation-based cell therapy faces two major difficulties for treating nerve injuries in human patients: (i) potential for tumor formation from undifferentiated stem cells exist in the injury site; (ii) significant time delay in preparation of stem cells for autologous transplantation, not optimal for functional improvement; and (iii) significant death of transplanted cells.

As an alternative to transplantation, reprogramming of endogenous non-neuronal cells, such as scar-forming fibroblasts/glia into neurons has been attempted. In this method, the fates of many somatic cells (in-vitro) are re-specified by the expression of few specific transcription factors. Neuronal conversion from human fibroblasts can be induced by lineage-specific transcription factors (6); however, the introduction of ectopic genes limits the therapeutic applications of such approach. Direct conversion of fibroblasts into neurons (bypassing the neural progenitor stage) has also been shown by different chemical cocktails of small molecules. However, current trans-differentiation technologies are limited by requirement of long trans-differentiation period.

To overcome the challenges, the present invention provides a nanomaterial-molecular composition for nano-enhanced Trans-differentiation (NCT) consisting different concentrations of: (i) Curcumin (HDAC inhibitor); (ii) 2,4-Dinitrophenol (cAMP enhancer), (iii) SB216763 (GSK3 inhibitor); (iv) SD-208 (TGFβ1 inhibitor); and (v) PD98059 (MEK inhibitor). Curcumin as HDAC inhibitor mediates reprogramming through various processes, such as histone deacetylation, transcription factor or regulator deacetylation followed by chromatin remodeling. Inhibition of TGF-β by SD-208, and inhibition of GSK-3 by SB216763 improves the conversion of fibroblasts to neurons by Ascl1 and Ngn2. 2,4-Dinitrophenol enables Ngn2 to convert human fibroblasts into neurons. PD98059 is non-ATP competitive MEK inhibitor, specifically inhibits MEK-1-mediated activation of MAPK and does not directly inhibit ERK1 or ERK2. Use of Nanomaterials including nanoparticles (spheres, rods, ellipsoids, pyramids) made of metal, semiconductor or insulators enhances trans-differentiation. Our nanomaterial-molecular composition was found to reduce the trans-differentiation period to <1 week.

Further, different combinations of lineage-specific transcription factors could directly convert fibroblasts, hepatocytes (18) and cardiomyocytes (19) from somatic cells bypassing the pluripotent state. Notably, adult pancreatic exocrine cells and cardiac fibroblasts (in injured adult mouse heart) could be directly transformed in-vivo into insulin secreting cells and cardiomyocytes respectively. Recent studies also showed the potential of directly converting astrocytes to neurons. However, current trans-differentiation technologies are limited by low trans-differentiation efficiency. The present disclosure provides novel compositions, methods and devices for nano-enhanced opto-chemical trans-differentiation (NOCT) to achieve trans-differentiation of fibroblasts/glia to neurons with high efficiency. The use of light illumination enhances the delivery or release of molecular composition to the fibroblasts/glia via photothermal, photochemical activation of the nanomaterials. Further, use of biodegradable polymers such as PLGA as nanomaterials encapsulating the composition allows slow release of the entrapped molecular composition, thus enhancing the trans-differentiation efficiency and minimizing the injection frequency.

The current trans-differentiation technologies lack ability for spatially controlled trans-differentiation. In order to mitigate the challenges in spatially targeted trans-differentiation of cells and tissues (in-vitro or, in-vivo), the present disclosure provides novel nanomaterial-molecular efficient and targeted trans-differentiation of cells including fibroblasts and glia into neurons, both in vitro as well as in situ and in-vivo, which is of great importance for cell replacement therapies. In an embodiment, the NOCT method is meant for use of nanoparticles or nanostructures such as nano-rods, nano-ellipsoids, nano-prisms, nano-stars, nano-shells made out of metal such as gold, silver etc., semiconductors or insulators that can enhance local optical field by plasmon (metal-dielectric interface), exciton (in semiconductors) or phonon (in absorbing insulators) excitations, which triggers localized release of compositions for trans-differentiation and/r interacts with cells to enhance delivery of the said compositions for efficient trans-differentiation.

In another embodiment, the present invention provides a method for efficient and targeted NOCT of cells in-vitro, in-situ or in-vivo which comprises of a) providing functionalized nanomaterial-molecular compositions to a population of cells, whereby said nanomaterials binds to the cell type of interest; b) providing optical illumination of said population of cells with a light beam tuned to activation of said nanomaterials by photothermal, photochemical or photo-disruption, whereby said cell types bound by said functionalized nanomaterials allow release and/or delivery of said molecular compositions into said cell type. In addition, the invention in some aspects provides devices for targeted nano-enhanced opto-chemical trans-differentiation (NOCT) of fibroblasts/glia to neurons in the central and peripheral nervous system for restoration of neural functions in patients by actuating delivery of nanomaterial-molecular composition, followed by optical illumination.

By "nanomaterials" as used herein is meant nanoparticles or nanostructures such as nano-rods, nano-ellipsoids, nano-prisms, nano-stars, nano-shells made out of metal such as gold, silver etc., semiconductors or insulators that can enhance local optical field. In one embodiment nanoparticles that find use in the methods disclosed herein include but are not limited to gold nano-rods and By "optical illumination" as used herein is meant but not limited to any light source, LED, Laser beam preferably the NIR laser beam with a wavelength of 400-1500 nm and of power varying from 1 to 1000 mW focused to spots of size ranging from ~0.001 to 1 cm.

In one embodiment the nanomaterials are functionalized with a targeting agent using methods known in the art. By targeting agent is meant an agent that binds specifically with a target cell. Targeting agents can be ligands, antibodies, antibody fragments, nucleic acids, aptamers, small molecules and like, so long as the targeting agent is able to bind specifically to one cell type. In this way, once the nanomaterial-targeting agent complex is added to a mixture of cells, only the desired cell type will be associated with the nanomaterials.

In some embodiments, nanoparticles are functionalized in 2, 3, 4, 5, 10, 20, 50, 75, 100 or more distinct groups with 2, 3, 4, 5, 10, 20, 50, 75, 100 or more targeting agents to target 2, 3, 4, 5, 10, 20, 50, 75, 100 or more cell types, respectively.

The functionalized nanomaterials are then contacted with a cell type of interest or a plurality of cell types. Notably, however, the nanomaterials only bind to the cell type that is specific for the respective targeting agent. Accordingly, cells can be treated in vitro, ex vivo or in vivo.

In some embodiments, nanomaterials having different materials/shapes and therefore, specific plasmon/exciton/phonon resonance peaks can be used. For example, the aspect ratio (ratio of size of short axis to long axis) of gold nanoparticles can vary from 1:1 to 1:7 to result in SPR peak varying from visible to NIR (1100 nm). Nanomaterials having first and second characteristic materials/shapes and resonances can be functionalized with first and second targeting compositions to target different cells or can be used to release first and second agents to first (e.g., fibroblasts) and second (astrocytes) cell types.

Nanomaterial-molecular compositions to be administered to the respective cells can be added to a population or mixture of cells. The cells are then illuminated with a light beam having wavelength matching the peak of the plasmon/exciton/phonon resonance of the nanomaterial. It is thought that because the nanoparticle is in close proximity to the cell surface, as a result of the targeting agent, the plasmon/exciton/phonon resonance of the nanomaterial will allow release and/or delivery of said molecular compositions into said cell type the photothermal, photochemical or photo-disruption, whereby said cell types bound by said functionalized nanomaterials will be trans-differentiated without affecting the non-targeted cells. In some embodiments, a second nanomaterial-targeting agent complex is contacted with the cell mixture and a second molecular composition is administered to a second population of cells (e.g., astrocytes) by repeating the procedure.

The concentrations of each component (Curcumin, 2,4-Dinitrophenol, SB216763, SD-208, and PD98059) of the nanomaterials-molecular compositions can vary in the range preferably of 0.1 μM up to 300 μM. The nanomaterials with concentration ranging from 0.01 μg/ml to 100 μg/ml.

In an embodiment, the optical illumination proceeds preferably at average power of ~0.1 mW to 10 W (with a spot size of ~0.001 to ~1 cm) and may last from 1 sec to ~2 minutes. The optical illumination wavelength is in the range of 400 to 1500 nm, and the illumination is directed to the cells directly or via optical fiber, waveguides, lenses, mirrors and other beam steering/shaping devices. The optical illumination may be continuous or pulsed (width varying from several picoseconds to minutes, and repetition rate varying from 0.1 Hz to 200 MHz) in order to optimize trans-differentiation without observable heating/damage of the cells/tissues.

Once irradiation of the sample is complete the samples may be allowed to incubate with the nanomaterials-molecular compositions for varying periods of time preferably such as from 0.5 hour to 5 months, or from 1 hour to 2 months or from 2 hours to 1 month or from 5 hours to 30 days or from 10 hours to 10 days to around 30 hours to 5 days. In some embodiments, incubation proceeds for around 0.5 hours, around 1 hour, around 5 hours, around 10 hours, around 30 hours, around 60 hours, around 2 days, around 5 days, around 10 days, around 20 days, around 30 days, around 60 days, around 2 months, around 5 months, around 7 months, around 10 months or around 24 months.

This disclosure demonstrates the efficient and targeted nano-enhanced Opto-Chemical Trans-differentiation (NOCT) of cells in-vitro, in-situ or in-vivo which comprises of a) providing functionalized nanomaterial-molecular compositions to a population of cells, whereby said nanomaterials binds to the cell type of interest; and b) providing optical illumination of said population of cells with a light beam tuned to activation of said nanomaterials by photo-thermal, photochemical or photo-disruption, whereby said cell types bound by said functionalized nanomaterials allow release and/or delivery of said molecular compositions into said cell type. In addition, the disclosure achieves targeted nano-enhanced opto-chemical trans-differentiation (NOCT) of fibroblasts/glia to neurons by actuating delivery of nano-material-molecular composition, followed by optical illumination.

In some embodiments, the cells whose trans-differentiation can be enhanced by use of nanomaterials and optical illumination according the methods described herein include, but are not limited to fibroblasts, glia, Muller glia cells of retina, oligodendrocyte progenitors, astrocytes, adipose cells, endothelial, epithelial cells, keratinocytes, osteocytes, lipocytes, skeletal-muscle cells from different organs and sources including but not limited to different mammals including humans. In yet another embodiment, by use of nanomaterials and optical illumination according the methods described herein, these cells can be trans-differentiated into neurons including, but are not limited to myelinated, un-myelinated, dopaminergic, serotonergic, cholinergic, GABAergic, Glutamatergic, fast spiking, interneurons, purkinje, pyramidal, sensory, motor and autonomous neurons.

In yet another embodiment, this invention can be exploited to transdifferentiate Muller glia cells (which are great source of retinal stem cells) to replenish damaged retinal cells including photoreceptors and Retinal ganglion cells in order to restore vision.

In another embodiment, the molecular compositions whose trans-differentiation effect can be enhanced by use of nanomaterials and optical illumination according the methods described herein include, but are not limited to small molecules, transcription factors, HDAC inhibitors, cAMP, cAMP enhancers, GSK3 inhibitors, TGFb1 inhibitors, PKC inhibitors, p53 inhibitors, MEK inhibitors, ALK-inhibitors, ERK inhibitors, and Wnt modulators.

In one exemplary embodiment, the disclosed invention provides the method for the use of nano-enhanced opto-chemical trans-differentiation that does not cause either undesired trans-differentiation in non-targeted cells and organs, or any adverse reaction or cytotoxicity in the targeted region.

In some embodiments, the nanomaterial-molecular composition, NOCT method and device is used to convert fibroblasts into neurons, both in vitro as well as in situ and in-vivo, which is of great importance for cell replacement therapies. The disorders that find use of the compositions, methods and devices described herein include but not limited to strokes, TBI, nerve-machine interfaces, deep-brain-stimulation implant devices, neuro-degenerative brain disorders, spinal cord injury, and peripheral nerve injury, retinal degenerative diseases including but not limited to Retinitis Pigmentosa, Leber's congenital amaurosis, Dry-age related macular degeneration and Retinal Dystrophy.

The disclosure also provides design of several devices for performing NOCT, which comprise of a nanomaterial-molecular compositions delivery device, light source for optical illumination, integrated with a beam-steering arrangement and imaging camera in order to guide the molecular/optical illumination to area(s) of interest.

The disclosure also provides design of device for delivery of nanomaterial-molecular compositions for NOCT. The delivery device has reservoir containing/storing the said nanomaterial-molecular compositions for NOCT, mechanical actuation control for administering the said nanomaterial-molecular compositions in pre-decided intervals and durations, and tubing to guide the said nanomaterial-molecular compositions to the targeted area(s).

The disclosure includes design of device for delivery of optical illumination for NOCT, which comprises of a light source, whose intensity is controlled by attenuators and pulse-width by mechanical, electrical, optical or other means. It also includes scanning/beam-shaping components such as mirrors, light modulators and optical waveguides, that can be both implanted to deliver the light into deep tissue (if necessary) or integrated with other devices such as microscopes, endoscopes, surgical devices to illuminate the tissues of interest.

The disclosure also provides design of several electrical stimulation/recording devices from nano-enhanced opto-chemical trans-differentiated neurons comprising of metal/polymer electrode(s), optical waveguide(s), micropores/cannula for allowing delivery of light and nanomaterial-molecular compositions.

According to yet another aspect of the invention, the nanomaterial-molecular composition, NOCT method and device is used to convert fibroblast/glia in device-implanted area(s) of central or peripheral nervous systems into neurons and repeatedly used in case of re-appearance of fibroblast/glia.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a molecule or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Below, the presently disclosed invention will be further described by way of examples, which are provided for illustrative purposes only and accordingly are not to be construed as limiting the scope of the invention.

EXAMPLES

Example 1

Figure 1:
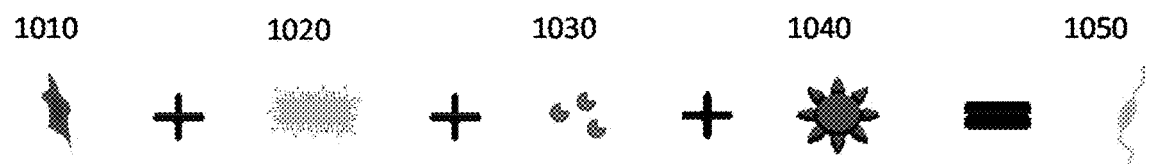
FIG. 1 depicts various components of Nano-enhanced Opto-Chemical Trans-differentiation (NOCT). 1000: identify target population of cells; 1010: Glia/fibroblast; 1020: Nanorods/nanoparticles; 1030: Chemicals; 1040: Light; and 1050: Trans-differentiated Neuron From Glia/Fibroblast.

FIG. 1 depicts various components of Nano-enhanced Opto-Chemical Trans-differentiation (NOCT). Target population of cells such as Glia/fibroblast (1010) identified to be trans-differentiated can be in an organ in-vivo or in-situ in a container.

The functionalized nanorods (1020) are designed to bind to targeted cell population.

The chemicals (1030) in the nanomaterial-molecular compositions are: (i) Curcumin (25 µM); (ii) 2,4-Dinitrophenol (10 µM), (iii) SB216763 (1 µM); (iv) SD-208 (1 µM); and (v) PD98059 (7 µM). The light (1040) is from a nanosecond 1064 nm laser source. The trans-differentiated neurons (1050) are generated in light-illuminated areas after 6 days.

Example 2

Figure 2:
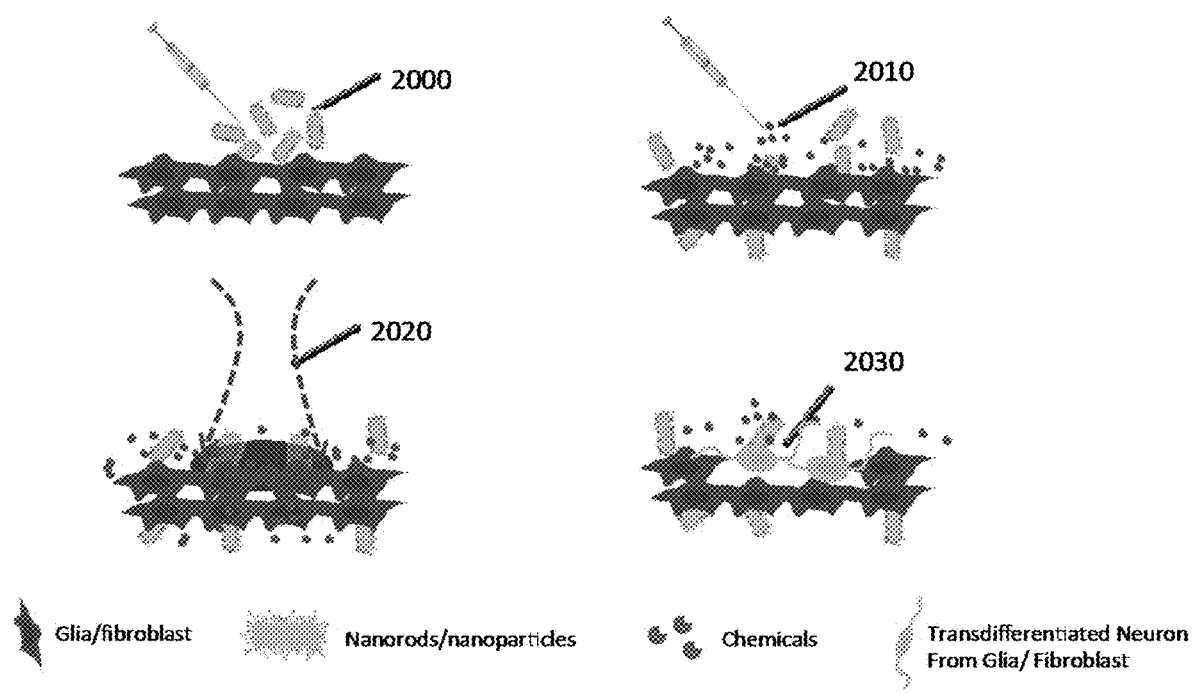
FIG. 2 shows various steps of the spatially targeted Nano-enhanced Opto-Chemical Trans-differentiation (NOCT). 2000: Add nanorods/nanoparticles functionalized for glia/fibroblasts; 2010: Functionalized nanorods/nanoparticles bind to targeted cells, add chemicals for trans-differentiation; 2020: Irradiate targeted area(s) with light/laser beam with wavelength tuned to SPR of nanorods/nanoparticles; 2030: Obtain localized trans-differentiated neurons with high-efficiency.

For spatially targeted nano-enhanced Opto-Chemical Trans-differentiation (NOCT) of different types of cells, gold nano-rods were synthesized. FIG. 2 shows the various steps of the spatially targeted NOCT of fibroblasts to neurons.

Step 1 (2000): The nanomaterial-molecular compositions containing gold nano-rods, functionalized to bind specific cells, are added/injected directly to extracellular medium or targeted organ such as brain, spinal cord, peripheral nerve, or indirectly via injection into circulatory system via intra-peritoneal, or intra-venous path.

Step 2 (2010): The functionalized gold nanomaterial-molecular compositions are allowed certain incubation period with the targeted cells.

Step 3 (2020): Optical illumination of said population of cells with a light beam tuned to activation of said nanomaterials to cause photothermal, photochemical or photo-disruption changes.

The sample or the beam is either scanned (by scanning mirrors or stages) or spatially modulated (for example by spatial light modulator or digital micro-mirror device) to cover the targeted area. Thus the release and/or delivery of said molecular compositions to targeted cell types (bound to the said functionalized nanomaterials) in the illuminated area occur.

While continuous exposure to light can be used to accomplish NOCT, the light may be pulsed (width varying from several picoseconds to minutes) in order to optimize NOCT without overall heating of the cells/tissues.

Step 4 (2030): After switching off the light beam, certain time period (hours to days or even several weeks) may be allowed for the molecular compositions activates/inhibits specific cellular machineries either to express or suppress desired activity for the trans-differentiation to occur. The said functionalized nanomaterial-molecular compositions to said population of cells may be delivered at intervals of 6 to 96 hrs for 1 to 30 days; and the said optical illumination of said population of cells may be provided at intervals of 6 to 96 hrs for 1 to 30 days. The structure/functioning of the trans-differentiated neurons can be examined by microscopy, endoscopy, electrophysiology, fMRI or behavioral assays.

Example 3

Figure 3:
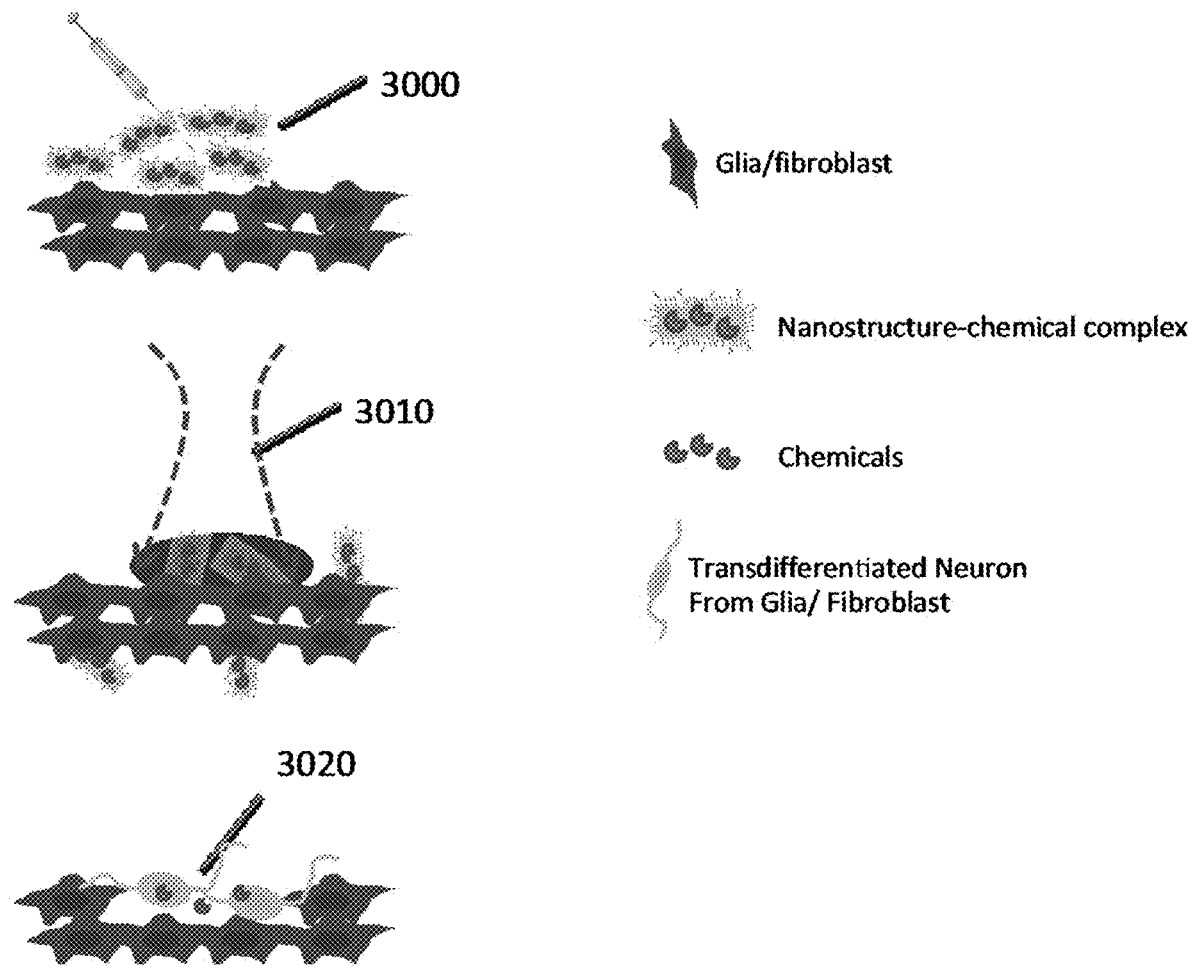
FIG. 3 shows various steps of the spatially targeted Nano-enabled Opto-Chemical Trans-differentiation (NOCT) using controlled release of chemicals from the nanostructure-chemical complexes. 3000: Add Nanostructure-chemical complexes functionalized for glia/fibroblasts; 3010: Functionalized nanostructure-chemical complexes bind to targeted cells, irradiate targeted area(s) with light/laser beam to release the chemicals from the nanostructures; and 3020: Obtain localized trans-differentiated neurons with high-efficiency.

FIG. 3 shows various steps of the spatially targeted Nano-enabled Opto-Chemical Trans-differentiation (NOCT). Nanostructure-chemical complexes are synthesized.

Step 1 (3000): The nanomaterial-molecular compositions containing gold nano-rods, functionalized to bind specific cells, are added/injected directly to extracellular medium or targeted organ such as brain, spinal cord, peripheral nerve, or indirectly via injection into circulatory system via intra-peritoneal, or intra-venous path.

Step 2 (3010): The functionalized gold nanomaterial-molecular compositions are allowed certain incubation period with the targeted cells. Functionalized nanostructure-chemical complexes bind to targeted cells, irradiate targeted area(s) with light/laser beam to release the chemicals from the nanostructures. Optical illumination of said population of cells with a light beam tuned to activation of said nanomaterials to cause photothermal, photochemical or photo-disruption changes. The sample or the beam is either scanned (by scanning mirrors or stages) or spatially modulated (for example by spatial light modulator or digital micro-mirror device) to cover the targeted area. Thus the release and/or delivery of said molecular compositions to targeted cell types (bound to the said functionalized nanomaterials) in the illuminated area occur.

While continuous exposure to light can be used to accomplish NOCT, the light may be pulsed (width varying from several picoseconds to minutes) in order to optimize NOCT without overall heating of the cells/tissues.

Step 3 (3020): After switching off the light beam, certain time period (hours to days or even several weeks) may be allowed for the molecular compositions activates/inhibits specific cellular machineries either to express or suppress desired activity for the trans-differentiation to occur. The said functionalized nanomaterial-molecular compositions to said population of cells may be delivered at intervals of 6 to 96 hrs for 1 to 30 days; and the said optical illumination of said population of cells may be provided at intervals of 6 to 96 hrs for 1 to 30 days. The structure/functioning of the trans-differentiated neurons can be examined by microscopy, endoscopy, electrophysiology, fMRI or behavioral assays.

Example 4

Figure 4:
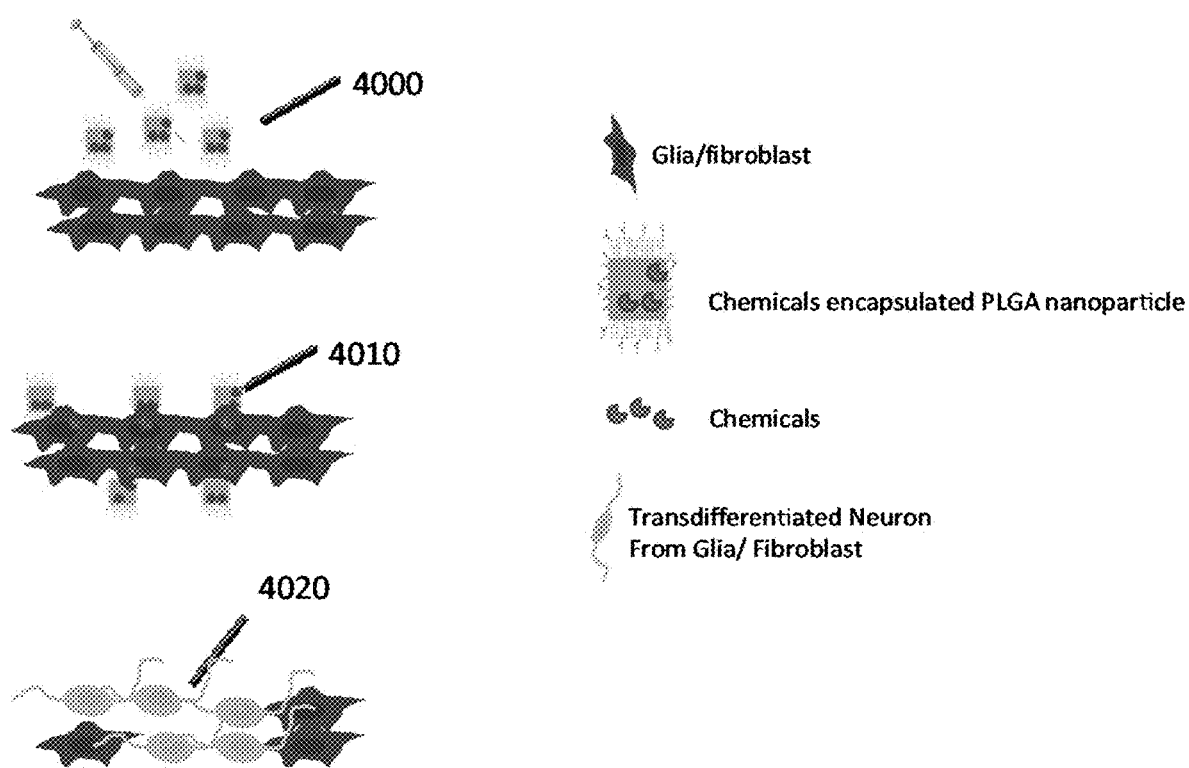
FIG. 4 depicts various steps of the Nano-enabled Chemical Trans-differentiation (NCT). 4000: Add Nanostructure-chemical complexes functionalized for glia/fibroblasts; 4010: Functionalized nanostructure-chemical complexes bind to targeted cells, chemicals slowly release from the PLGA nanoparticles; and 4020: Obtain trans-differentiated neurons with high-efficiency.

FIG. 4 shows various steps of the Nano-enabled Chemical Trans-differentiation (NCT) by use of chemical compositions encapsulated in PLGA nanomaterial for trans-differentiation of fibroblasts/glia to neurons and other cell types of interest.

Step 1 (4000): The PLGA Nanostructure-chemical complexes functionalized for glia/fibroblasts are added/injected directly to extracellular medium or targeted organ such as brain, spinal cord, peripheral nerve, or indirectly via injection into circulatory system via intra-peritoneal, or intravenous path.

Step 2 (4010): Chemicals from the functionalized nanostructure-chemical complexes slowly release and delivered to the targeted cells bound with the PLGA nanoparticles. Certain time period (hours to days or even several weeks) may be allowed for the molecular compositions activates/inhibits specific cellular machineries either to express or suppress desired activity for the trans-differentiation to occur.

Step 3 (4020): The structure/functioning of the trans-differentiated neurons can be examined by microscopy, endoscopy, electrophysiology, fMRI or behavioral assays. The efficiency of the trans-differentiation process can be optimized by delivering the said functionalized nanomaterial-molecular compositions to said population of cells at intervals of 1 to 14 days for 1 to 90 days.

Figure 5A:
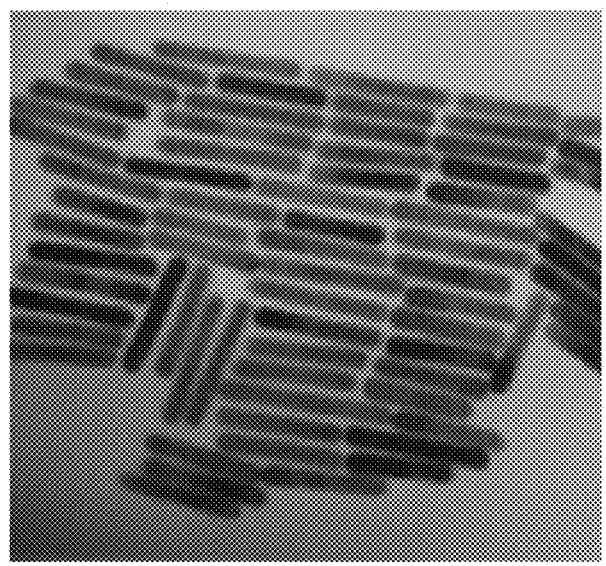
FIG. 5A shows high magnification electron microscopic image of gold nanorods used for optical enhancement of laser beam at the ends of the rods to cause efficient trans-differentiation of targeted fibroblasts/glia cells. These nanorods are functionalized with Concavalin A for target-specific binding fibroblasts.
Figure 5B:
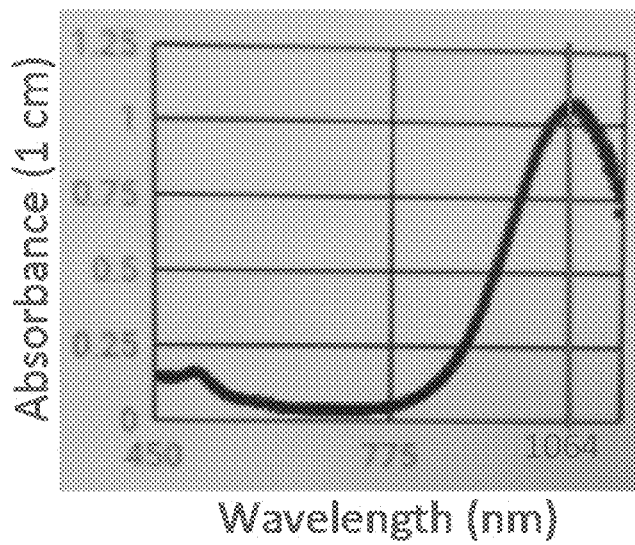
FIG. 5B shows the measured Optical density of the gold nanorods showing peak at 1064 nm.

Example 5 here, we show an example of use of gold nano-rods and NIR laser beam. FIG. 5A shows high magnification electron microscopic image of gold nanorods used for optical enhancement of laser beam at the ends of the rods to cause efficient trans-differentiation of targeted fibroblasts/glia cells. These nanorods are functionalized with Concavalin A for target-specific binding fibroblasts. Varying shape of these gold nano-rods allowed wavelength-selective Surface Plasmon enhancement. FIG. 5B shows the measured optical density of gold nano-rods showing resonance peak at 1064 nm. Tuning the NIR laser wavelength allowed selective NOCT of targeted population of cells.

Example 6

Next, we show the use of gold nano-rods and NIR laser beam (1064 nm) for NOCT of fibroblasts to neurons. FIG. 6A shows image of immunostained (Blue: DAPI; Red: βIII tubulin) fibroblast cells treated with nanomaterial-molecular compositions consisting: Curcumin; 2,4-Dinitrophenol; SB216763; SD-208; PD98059 and gold nanorods. Without use of laser, significant number of non-transdifferentiated fibroblasts was observed as evidenced by βIII tubulin staining (marker for neurons). FIG. 6B shows the image of immunostained (Blue: DAPI; Red: βIII tubulin) fibroblast cells treated with same nanomaterial-molecular compositions (Curcumin; 2,4-Dinitrophenol; SB216763; SD-208; PD98059 and gold nanorods) along with nanosecond near-infrared (1064 nm) laser beam treatment at intervals of 1 day for 5 days. Highly efficient trans-differentiation to neurons was observed in the laser-treated samples (FIG. 6B) as compared to the untreated samples (FIG. 6A).

Example 7

Figure 7:
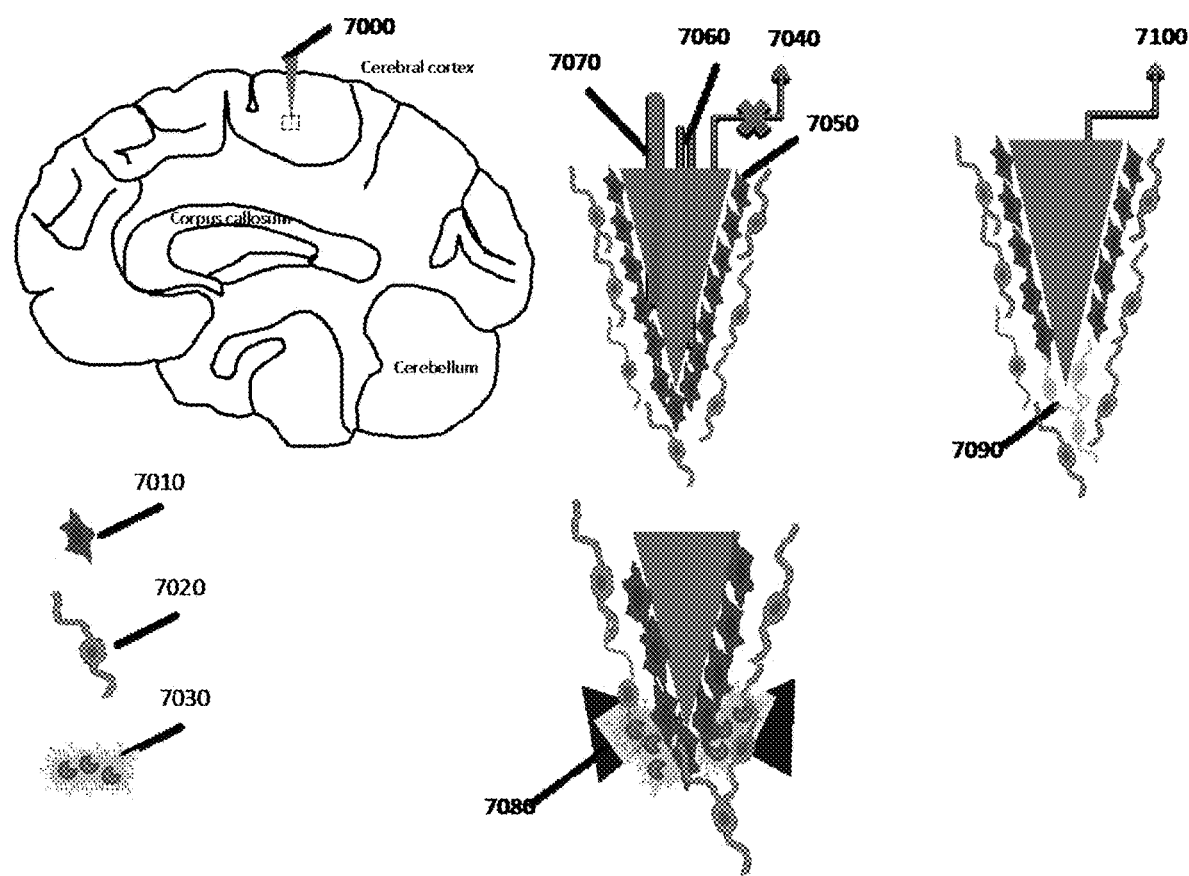
FIG. 7 illustrates various components of the device and method for spatially targeted Nano-enhanced Opto-Chemical Trans-differentiation (NOCT) in brain. 7000: Implant; 7010: Glia/Fibroblast; 7020: Neuron; 7030: Nanostructures/chemicals; 7040: Electrode(s) for electrical stimulation/detection; 7050: Neural activity measurement and/or stimulation is blocked by glia/fibroblast scar; 7060: Cannula port for delivery of fluid containing chemicals and/or nano-materials; 7070: Optical fiber for light delivery/signal detection; 7080: Light illumination (400-1500 nm); 7090: Transdifferentiated Neuron from Glia/Fibroblast; and 7100: Neural activity measurement/stimulation is allowed via trans-differentiated neurons from glia/fibroblasts using NOCT.

FIG. 7 illustrates the various components of the device and method for spatially targeted Nano-enhanced Opto-Chemical Trans-differentiation (NOCT) in brain. In this method trans-differentiation of fibroblast/glial scar (7010, 7050) formed around implant (7000) to functional neurons (7090) in the brain is achieved by delivering the nanomaterial-molecular compositions (7030) via a cannula (7060) and laser irradiation (7080) by optical fiber (7070). The reservoir containing/storing the said nanomaterial-molecular compositions is connected to the cannula via tubing to guide the said nanomaterial-molecular compositions to the targeted area(s). The method and device for NOCT in brain also includes mechanical actuation control for administering the said nanomaterial-molecular compositions in pre-decided intervals and durations. Further to enable neural activity measurement and/or stimulation (7100), blocked by glia/fibroblast scar (7050), the cannula is made through or along the electrode(s) used for electrical stimulation/detection. The Optical fiber (7070) can be inserted through the cannula (7060) for light delivery and/or detection of back-scattered signal for structural/functional analysis. After delivery of nanomaterial-chemical compositions, when a visible/near-infrared (NIR) laser beam in the range of 400 to 1500 nm (at average illumination power in the range of 0.1 mW to 10 W) is directed to the brain scar regions bound to nanomaterials via the optical fiber, trans-differentiation of the scar tissue to neurons occur. The optical illumination for NOCT comprises of: light source, whose intensity is controlled by attenuators and pulse-width by mechanical, electrical, optical or other means, scanning/shaping the illumination by mirrors, light modulators and optical waveguide arrays, implantable waveguides to deliver the light into deep tissue (if necessary). In this method, targeted nano-enhanced opto-chemical trans-differentiation (NOCT) does not cause either undesired trans-differentiation in non-targeted cells and organs, or any adverse reaction or cytotoxicity in the targeted region. Furthermore, the NOCT of scar tissue can be carried out in case of re-appearance of fibroblast/glia in injured/implanted area(s). Notably, using this device and method NOCT of cells can be carried out with other molecular compositions of small molecules and/or genes.

Example 8

Figure 8:
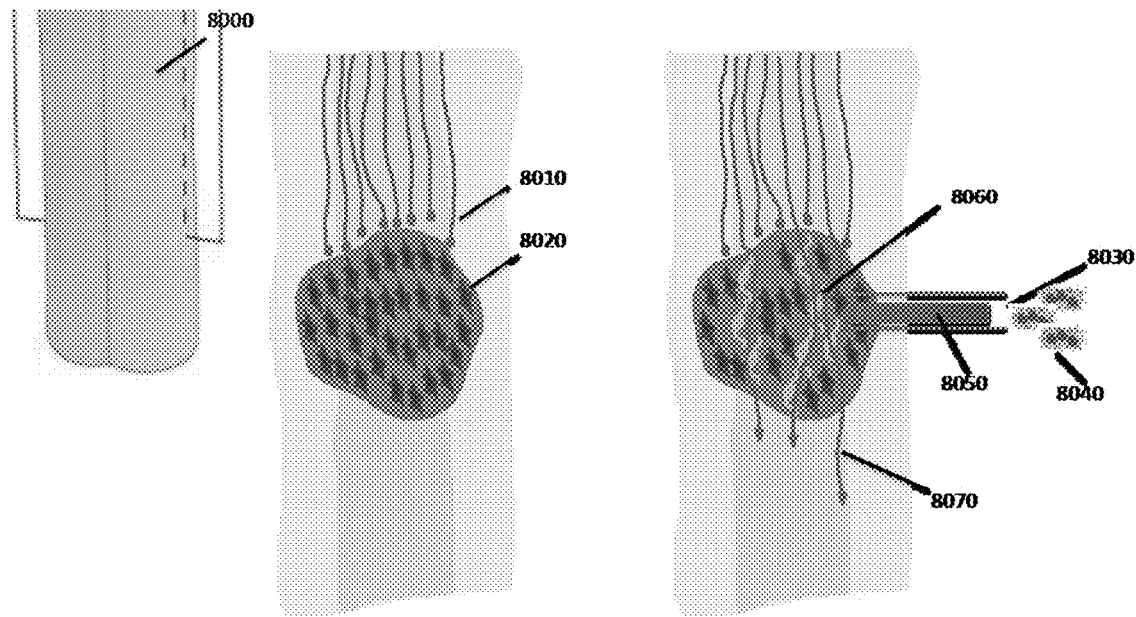
FIG. 8 depicts various components of the device and method for spatially targeted Nano-enhanced Opto-Chemical Trans-differentiation (NOCT) in spinal cord. 8000: Schematic of sagittal section of spinal cord; 8010: Injured axons; 8020: Glia/Fibroblast scar; 8030: Cannula port for delivery of fluid/optical fiber; 8040: Fluid containing chemicals and/or nano-materials; 8050: Optical fiber for light delivery; 8060: Transdifferentiated Neuron from Glia/Fibroblast.

FIG. 8 shows various components of the device and method for spatially targeted Nano-enhanced Opto-Chemical Trans-differentiation (NOCT) in spinal cord. The device and method is used for NOCT of fibroblast/glial scars formed in injured spinal cord to functional neurons. In this method trans-differentiation of fibroblast/glial scar (8020) (formed around injured axons (8010)) to functional neurons (8060) in the spinal cord is achieved by delivering the nanomaterial-molecular compositions (8040) via a cannula (8030) and laser irradiation by optical fiber (8050). The reservoir containing/storing the said nanomaterial-molecular compositions is connected to the cannula via tubing to guide the said nanomaterial-molecular compositions to the targeted area(s). The method and device for NOCT in the spinal cord also includes mechanical actuation control for administering the said nanomaterial-molecular compositions in pre-decided intervals and durations. The Optical fiber (8050) can be inserted through the cannula (8030) for light delivery and/or detection of back-scattered signal for structural/functional analysis. After delivery of nanomaterial-chemical compositions, when a visible/near-infrared (NIR) laser beam in the range of 400 to 1500 nm (at average illumination power in the range of 0.1 mW to 10 W) is directed to the scar regions bound to nanomaterials via the optical fiber, trans-differentiation of the scar tissue (8020) to neurons (8060) occurs. This facilitates regeneration and growth of axons of injured neurons (8010) via the newly trans-differentiated neurons (8060). Further, the injured neurons (8010) will create synapses with the newly trans-differentiated neurons (8060), and the newly trans-differentiated neurons (8060) will grow along the spinal tracts toward target sites. The optical illumination for NOCT comprises of: light source, whose intensity is controlled by attenuators and pulse-width by mechanical, electrical, optical or other means, scanning/shaping the illumination by mirrors, light modulators and optical waveguide arrays, implantable waveguides to deliver the light into deep tissue (if necessary). In this method, targeted NOCT does not cause either undesired trans-differentiation in non-targeted cells and organs, or any adverse reaction or cytotoxicity in the targeted region or aberrant inputs with other neurons. Furthermore, the NOCT of scar tissue can be carried out in case of re-appearance of fibroblast/glia in injured area(s). Notably, using this device and method NOCT of cells can be carried out with other molecular compositions of small molecules and/or genes.

Example 9

One of the examples where the method is used for nano-enhanced opto-chemical trans-differentiation of fibroblast scars formed around electrode-nerve implants (for nerve-machine interface) in the peripheral nervous system to functional neurons. FIG. 9 represents various components of the device and method for spatially targeted Nano-enhanced Opto-Chemical Trans-differentiation (NOCT) in peripheral nervous system. In this method trans-differentiation of fibroblast/glial scar (9040) formed around implanted electrode-nerve interface (9010) to functional (motor/sensory) neurons (9080) in the peripheral nerve is achieved by delivering the nanomaterial-molecular compositions via a cannula (9050) and laser irradiation (9070) by optical fiber (9060). The reservoir containing/storing the said nanomaterial-molecular compositions is connected to the cannula via tubing to guide the said nanomaterial-molecular compositions to the targeted area(s). The method and device for NOCT in peripheral nerve also includes mechanical actuation control for administering the said nanomaterial-molecular compositions in pre-decided intervals and durations. Further to enable neural activity measurement and/or stimulation (9030), blocked by glia/fibroblast scar (9040), the cannula is made through or along the electrode(s) used for electrical stimulation/detection. The Optical fiber (9060) can be inserted through the cannula (9050) for light delivery and/or detection of back-scattered signal for structural/functional analysis. After delivery of nanomaterial-chemical compositions, when a visible/near-infrared (NIR) laser beam in the range of 400 to 1500 nm (at average illumination power in the range of 0.1 mW to 10 W) is directed to the scar regions bound to nanomaterials via the optical fiber, trans-differentiation of the scar tissue to neurons occur. Further, the newly trans-differentiated neurons (9080) will create synapses with the endogenous neurons (9020) allowing recording/stimulation (9090) of targeted motor/sensory axons using the implanted electrode-nerve interface (9010). The optical illumination for NOCT comprises of: light source, whose intensity is controlled by attenuators and pulse-width by mechanical, electrical, optical or other means, scanning/shaping the illumination by mirrors, light modulators and optical waveguide arrays, implantable waveguides to deliver the light into deep tissue (if necessary). The electrical stimulation/recording device from nano-enhanced optochemical trans-differentiated neurons comprises of: metal/polymer electrode(s), optical waveguide(s), and micropores/cannula for allowing delivery of light and nanomaterial-molecular compositions. In this method, targeted NOCT does not cause either undesired trans-differentiation in non-targeted cells and organs, or any adverse reaction or cytotoxicity in the targeted region or aberrant inputs with endogenous axons. Furthermore, the NOCT of scar tissue can be carried out in case of re-appearance of fibroblast/glia in injured/implanted area(s). Notably, using this device and method NOCT of cells can be carried out with other molecular compositions of small molecules and/or genes.

Example 10

FIG. 10 shows the various steps of the spatially targeted in-situ Nano-enhanced Opto-Chemical Trans-differentiation (NOCT) of Mueller Glial cells to photosensitive retinal cells in retina. In case of retinal degenerative diseases such as Retinitis Pigmentosa, dry-age related macular degeneration, in the areas of degenerated/scarred retina (10010), the natural photoreceptors (10060) are non-functional or degenerated. In such cases, Nanoparticles and chemicals (10030) are intraocular delivered by needle-syringe or shunt device (10020) once or in a repeated manner manually or in a controlled manner. The visible/near-infrared (400-1500 nm) Laser beam (10040) is used in-situ to activate the nanomaterial and help trans-differentiate the Muller-Glial cells (10050) to photosensitive retinal cells (10070). Upon exposure to visual stimulation (ambient light or active projection of image), the trans-differentiated photosensitive retinal cells will convert the visual stimulation to electrical signal which is transmitted via optic nerve to the visual cortex for vision restoration.

Example 11

One of the examples where the method is used for In-situ opto-chemical trans-differentiation of trans-differentiation of Muller-Glial cells to partially trans-differentiated photoreceptors (ptdPRs). FIG. 11A shows in-situ trans-differentiation of Muller Glial cells to partially trans-differentiated photoreceptor like cells (ptdPRs) in rd1 mice eye treated with nanomaterial-molecular compositions consisting: Curcumin; 2,4-Dinitrophenol; SB216763; SD-208; PD98059 and gold nanorods at intervals of 1 day for 5 days. Nuclei are stained with DAPI (blue) and partially trans-differentiated PRs in retina are immunostained with visual arrestin antibody (green). Partial trans-differentiation to photoreceptors was observed in the treated eye (FIG. 11A) as compared to the untreated eye. FIG. 11B shows the negative control showing retinal cell nuclei stained with DAPI (blue) and absence of photoreceptor like cells (visual arrestin in green) in rd1 mice.

Example 12

FIG. 12 shows various steps of the spatially targeted in-situ Nano-enhanced Opto-Chemical Trans-differentiation (NOCT) of fibroblasts to photoreceptors in retina. In case of retinal degenerative diseases such as Retinitis Pigmentosa, dry-age related macular degeneration, in the areas of degenerated/scarred retina (12010), the natural photoreceptors (12060) are degenerated. Fibroblasts (12050) are known to accumulate in scarred retina in the sub-retinal space. In such cases, Nanoparticles and chemicals (12030) are intraocular delivered by needle-syringe or shunt device (12020) once or in a repeated manner manually or in a controlled manner. The visible/near-infrared (400-1500 nm) Laser beam (12040) is used in-situ to activate the nanomaterial and help trans-differentiate the fibroblasts (12050) to photoreceptors (12070). Upon exposure to visual stimulation (ambient light or active projection of image), the trans-differentiated photoreceptors will convert the visual stimulation to electrical signal that is transmitted via optic nerve to the visual cortex for vision restoration.

Example 13

One of the examples where the method is used for In-situ nano-enhanced opto-chemical trans-differentiation of trans-differentiation of Muller cells to Trans-differentiated photoreceptors (tdPRs). FIG. 13 shows the In-situ trans-differentiation of Muller cells to Trans-differentiated photoreceptors (tdPRs) in rd1 mice eye treated with nanomaterial-molecular compositions consisting: Curcumin; 2,4-Dinitrophenol; SB216763; SD-208; PD98059 and gold nanorods at intervals of 1 day for 5 days. Trans-differentiated PRs in retina is visualized by immunostaining the retina with visual arrestin antibody (Blue: DAPI; Green: Visual arrestin) after 7 days of final injection. Highly efficient trans-differentiation to photoreceptors was observed in the treated eye (FIG. 13) as compared to the untreated eye.

Example 14

One of the examples where In-situ nano-enhanced opto-chemical trans-differentiation (NOCT) is achieved using a device. FIG. 14 shows the schematic of the integrated laser for NOCT (14000) and optical coherence tomographic (OCT) imaging system for fundoscopic examination and targeting of specific layers of the degenerated retinal areas. The OCT system consists of a NIR low coherence source (14070), which is routed through a Circulator (14080) into a 2×2 Fiber coupler (14010). The NIR laser (14000) for NOCT, selected to have a wavelength spectrally separated from that of the OCT source, is coupled to the second input channel of the fiber coupler (14010). The NOCT laser beam (400-1500 nm) emanating from the out put of the fiber coupler is collimated by a collimating lens (14020) and targeted to selected retinal areas by scanning mirrors (14030, 14040) and pair of telescopic lenses (14050, 14060). During identification of retinal pathology, the visible/NIR (400-1500 nm) laser beam for NOCT is switched off. The beam from the low-coherence source (for OCT), at the output end of FC is collimated by the same collimating lens (14020) and scanned by the pair of mirrors (14030, 14040). The OCT beam is delivered to the eye by use of telescopic lenses (14050, 14060). The reference beam emanating from the other port of the fiber coupler is collimated by another collimating lens (14090) and reflected back via the same port by use of reference mirror (14100) as shown in FIG. 14. The back-reflected sample beam from the eye (and retina) and the reference beam are routed back via the circulator (14080) to a spectrometer, which comprises of grating (14120) and lenses (14130, 14140). The interferrogram is recorded in a camera (14150) and processed to obtain structural information of the eye and retina in particular, indicating its pathological condition. The layers/regions of interest for NOCT will be marked on the image displayed on the viewing screen (14160).

The visible/NIR light beam (used for NOCT) may have absorption in neural tissues. To minimize temperature rise (which may elicit damage to tissue), the NOCT laser beam can be pulsated and the duty cycle is varied to achieve optimal effect. For example, the optical illumination may be continuous or pulsed (width varying from several picoseconds to minutes, and repetition rate varying from 0.1 Hz to 200 MHz) in order to optimize trans-differentiation without observable heating/damage of the cells/tissues.

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth above, are specifically incorporated by reference.

1. Lin Cui et al., "Transplantation of Embryonic Stem Cells Improves Nerve Repair and Functional Recovery after Severe Sciatic Nerve Axotomy in Rats," *Stem Cells* 26, no. 5 (2008): 1356-65.
2. Peter Riess et al., "Transplanted Neural Stem Cells Survive, Differentiate, and Improve Neurological Motor Function after Experimental Traumatic Brain Injury," *Neurosurgery* 51, no. 4 (2002): 1043-54.
3. Walter Heine et al., "Transplanted Neural Stem Cells Promote Axonal Regeneration through Chronically Denervated Peripheral Nerves," *Experimental Neurology* 189, no. 2 (2004): 231-40.
4. John W McDonald et al., "Transplanted Embryonic Stem Cells Survive, Differentiate and Promote Recovery in Injured Rat Spinal Cord," *Nature Medicine* 5, no. 12 (1999): 1410.
5. Xinxin Han et al., "Efficient and Fast Differentiation of Human Neural Stem Cells from Human Embryonic Stem Cells for Cell Therapy," *Stem Cells International* 2017 (2017).
6. Thomas Vierbuchen et al., "Direct Conversion of Fibroblasts to Functional Neurons by Defined Factors," *Nature* 463, no. 7284 (2010): 1035.
7. Esther Y Son et al., "Conversion of Mouse and Human Fibroblasts into Functional Spinal Motor Neurons," *Cell Stem Cell* 9, no. 3 (2011): 205-18.
8. Xiang Li et al., "Small-Molecule-Driven Direct Reprogramming of Mouse Fibroblasts into Functional Neurons," *Cell Stem Cell* 17, no. 2 (2015): 195-203.
9. Yanqin Li et al., "Generation of IPSCs from Mouse Fibroblasts with a Single Gene, Oct4, and Small Molecules," *Cell Research* 21, no. 1 (2011): 196.
10. Lin Cheng et al., "Generation of Neural Progenitor Cells by Chemical Cocktails and Hypoxia," *Cell Research* 24 (Mar. 18, 2014): 665.
11. M Baranek et al., "Effect of Small Molecules on Cell Reprogramming," *Molecular BioSystems* 13, no. 2 (2017): 277-313.
12. Danwei Huangfu et al., "Induction of Pluripotent Stem Cells by Defined Factors Is Greatly Improved by Small-Molecule Compounds," *Nature Biotechnology* 26 (Jun. 22, 2008): 795.
13. Eva C Thoma et al., "Chemical Conversion of Human Fibroblasts into Functional Schwann Cells," *Stem Cell Reports* 3, no. 4 (2014): 539-47.
14. Yu Zhang et al., "Small Molecules, Big Rolesthe Chemical Manipulation of Stem Cell Fate and Somatic Cell Reprogramming," *J Cell Sci* 125, no. 23 (2012): 5609-20.
15. Wenxiang Hu et al., "Direct Conversion of Normal and Alzheimer's Disease Human Fibroblasts into Neuronal Cells by Small Molecules," *Cell Stem Cell* 17, no. 2 (2015): 204-12.
16. Xin Xie, Yanbin Fu, and Jian Liu, "Chemical Reprogramming and Transdifferentiation," *Current Opinion in Genetics & Development* 46 (2017): 104-13.
17. Wang P J. Chen S Q, Huang M, Liu C L, Shen Y Y, Cai Q, "Differentiation of Induced Pluripotent Stem Cells into Neural Stem Cells Induced by Brain-Derived Neurotrophic Factor via Wnt/β-Catenin and Extracellular Signal-Regulated Kinase/Mitogen-Activated Protein Kinases Signal Pathway," *Zhonghua Yi Xue Za Zhi* 97, no. 41 (2017): 3263-68.
18. Sayaka Sekiya and Atsushi Suzuki, "Direct Conversion of Mouse Fibroblasts to Hepatocyte-like Cells by Defined Factors," *Nature* 475, no. 7356 (2011): 390.
19. Jem A Efe et al., "Conversion of Mouse Fibroblasts into Cardiomyocytes Using a Direct Reprogramming Strategy," *Nature Cell Biology* 13, no. 3 (2011): 215.

What is claimed is:

1. A nanomaterial-molecular composition consisting of:
    a) a HDAC inhibitor consisting of Curcumin,
    b) a cAMP enhancer consisting of 2,4-Dinitrophenol,
    c) a GSK3 inhibitor consisting of SB216763,
    d) a TGF3 inhibitor consisting of SD-208,
    e) a MEK inhibitor c consisting of PD98059, and
    f) nanomaterials consisting of nanoparticles, nanostructures, semiconductor or insulators.

2. A method for targeted nano-enhanced opto-chemical trans-differentiation of cells comprising the steps of:
    a) providing a nanomaterial-molecular composition of claim 1 to a target population of cells, whereby said nanomaterials in the composition bind to the targeted cell type;
    b) providing optical illumination of said population of cells with a light beam to activate said nanomaterials in the composition of claim 1 by photothermal, photochemical or photo-disruption, whereby said targeted cell types bound by said nanomaterials allow release and/or delivery of said molecular compositions into said cell type;
    c) providing said composition of claim 1 to said population of cells at intervals of 6 to 96 hrs. for 1 to 30 days; and
    d) providing said optical illumination of said population of cells at intervals of 6 to 96 hrs. for 1 to 30 days; wherein said targeted cells are non-neuronal or non-stem cells in the central or peripheral nervous system (CNS or PNS).

3. The method according to claim 2, wherein said targeted cells are fibroblasts and/or glia.

4. The method according to claim 2, wherein the target cells are the cells in the fibroblast/glial scars formed around an implant in the CNS or PNS.

5. The method according to claim 2, wherein the target cells are the cells in the fibroblast/glial scars formed in injured spinal cord.

6. The method according to claim 2, wherein the target cells are Mueller-glial cells of the photoreceptor degenerated retina in subjects with retinal degenerative diseases comprising Retinitis Pigmentosa, Leber's congenital amaurosis, Dry-age related macular degeneration or Retinal dystrophy.

7. The method of claim 2, wherein the optical illumination wavelength is in the range of 400 to 1500 nm at average illumination power in the range of 0.1 mW to 10 W, and the illumination is directed to the cells directly or via optical fiber, waveguides, lenses, and/or mirrors.

8. The method of claim 2, wherein the optical illumination is by a continuous or pulsed laser.

9. The method according to claim 2, wherein the targeted nano-enhanced opto-chemical trans-differentiation does not cause either undesired trans-differentiation in non-targeted cells and organs, or any adverse reaction or cytotoxicity in the targeted region.

10. The method of claim 2, wherein the nano-enhanced opto-chemical trans-differentiation of cells is performed due to re-appearance of fibroblast/glia in injured/implanted area(s).

11. The method according to claim 2, wherein said target cells are in an in-vitro setting or in the tissue of an organ in-culture or in a living subject.

12. The method according to claim 11, wherein the in-vitro neurons are injected into the injured sites of the subject having injury to peripheral or central nervous system.

* * * * *